United States Patent
Nazzaro et al.

(10) Patent No.: US 10,599,181 B2
(45) Date of Patent: Mar. 24, 2020

(54) AUXILIARY ELECTRONIC DEVICE ATTACHABLE TO A WEARABLE ELECTRONIC DEVICE

(71) Applicant: Apple Inc., Cupertino, CA (US)

(72) Inventors: David I. Nazzaro, Groveland, MA (US); Tyler S. Bushnell, Mountain View, CA (US); Javier Mendez, San Jose, CA (US)

(73) Assignee: Apple Inc., Cupertino, CA (US)

( * ) Notice: Subject to any disclaimer, the term of this patent is extended or adjusted under 35 U.S.C. 154(b) by 188 days.

(21) Appl. No.: 15/922,769

(22) Filed: Mar. 15, 2018

(65) Prior Publication Data

US 2018/0203482 A1      Jul. 19, 2018

Related U.S. Application Data

(63) Continuation of application No. 14/632,924, filed on Feb. 26, 2015, now Pat. No. 9,946,297.
(Continued)

(51) Int. Cl.
  *G06F 1/16* (2006.01)
  *H02J 50/10* (2016.01)
  (Continued)

(52) U.S. Cl.
  CPC ............. *G06F 1/163* (2013.01); *A61B 5/681* (2013.01); *G04C 10/00* (2013.01); *G04G 19/10* (2013.01);
  (Continued)

(58) Field of Classification Search
  CPC . G06F 1/163; H02J 50/10; H02J 5/005; H02J 7/0044; H02J 7/025; H02J 17/00;
  (Continued)

(56) References Cited

U.S. PATENT DOCUMENTS 6,749,122 B1    6/2004  Koenck et al.
8,207,906 B2    6/2012  Tiscareno et al.
(Continued)

FOREIGN PATENT DOCUMENTS

WO    WO-2012/152980 A1    11/2012

OTHER PUBLICATIONS

Leclair, "Qimini Deuce mixes portable battery pack and wireless charger," Gizmag, Sep. 22, 2014, retrieved from http://www.gizmag.com/qimini-deuce-portable-wireless-charger/33917, 2 pages.
(Continued)

*Primary Examiner* — Carlos Amaya
(74) *Attorney, Agent, or Firm* — Morgan, Lewis & Bockius LLP (57) ABSTRACT

An auxiliary electronic device attachable to a wearable electronic device. The auxiliary device includes a housing, electronic circuitry within the housing, and an attachment mechanism configured to attach the auxiliary electronic device to the wearable device while the device is being worn by a user. In some embodiments the electronic circuitry includes a power transmitting unit that can wirelessly transmit power to charge a rechargeable battery within the wearable electronic device. In some embodiments the attachment mechanism includes a pair of lugs that extend, from opposite ends of the housing, above the housing towards a center of the auxiliary device and are adapted to fit within corresponding recesses of the wearable electronic device.

20 Claims, 7 Drawing Sheets

Related U.S. Application Data (60) Provisional application No. 62/057,531, filed on Sep. 30, 2014.

(51) Int. Cl.
  *G04C 10/00* (2006.01)
  *A61B 5/00* (2006.01)
  *H02J 5/00* (2016.01)
  *H02J 7/02* (2016.01)
  *H02J 7/00* (2006.01)
  *G04G 19/10* (2006.01)
  *G04G 21/02* (2010.01)
  *G04G 21/04* (2013.01)

(52) U.S. Cl.
  CPC ............ *G04G 21/02* (2013.01); *G04G 21/025* (2013.01); *G04G 21/04* (2013.01); *H02J 5/005* (2013.01); *H02J 7/0044* (2013.01); *H02J 7/025* (2013.01); *H02J 50/10* (2016.02)

(58) Field of Classification Search
  CPC ........ A61B 5/681; G04C 10/00; G04G 19/10; G04G 21/02; G04G 21/025; G04G 21/04
  See application file for complete search history.

(56) References Cited

U.S. PATENT DOCUMENTS

| | | |
|---|---|---|
| 2012/0153740 A1 | 6/2012 | Soar |
| 2013/0063873 A1 | 3/2013 | Wodrich et al. |
| 2014/0241555 A1 | 8/2014 | Terlizzi |
| 2015/0091388 A1 | 4/2015 | Golko et al. |
| 2015/0102879 A1 | 4/2015 | Jacobs et al. |
| 2015/0349571 A1 | 12/2015 | Wagman et al. |
| 2016/0056664 A1 | 2/2016 | Partovi |
| 2016/0062392 A1 | 3/2016 | Townsend et al. |
| 2016/0070393 A1 | 3/2016 | Sharma et al. |
| 2016/0325143 A1* | 11/2016 | Yuen .................... G01P 7/00 |

OTHER PUBLICATIONS

International Search Report and Written Opinion from PCT/US/2015/044571, dated Feb. 23, 2016, 17 pages.

\* cited by examiner

AUXILIARY ELECTRONIC DEVICE ATTACHABLE TO A WEARABLE ELECTRONIC DEVICE

CROSS-REFERENCES TO RELATED APPLICATIONS

This application is a continuation of U.S. patent application Ser. No. 14/632,924, filed Feb. 26, 2015, which is a nonprovisional patent application of and claims the benefit to U.S. Provisional Application No. 62/057,531 filed Sep. 30, 2014, the disclosures of which are hereby incorporated herein by reference in their entirety.

FIELD

The present invention relates generally to wearable electronic devices. More particularly, some embodiments of the invention relate to a device that can attach to and charge a wearable electronic device and/or provide additional functionality to the wearable electronic device while the wearable device is being worn by a user.

BACKGROUND

A variety of wearable electronic devices have been developed recently that include one or more sensors to measure various characteristics of the environment the device operates in. For example, electronic devices that can be worn on a user's wrist and do much more than act as a simple time piece are growing in popularity. Such devices may include a display to indicate the time and date. The devices may also include accelerometers and one or more sensors that enable a user to track fitness activities and health-related characteristics, such as heart rate, blood pressure, and body temperature, among other information. The devices also typically include a rechargeable battery that powers the electronics within the device.

Battery life is an important consideration for such wearable devices as the devices may not function properly without sufficient battery power. One manner in which the rechargeable battery within a wearable device can be charged is by connecting the device to a dedicated charger such as a docking station or charging stand much the same way a user may charge a smart phone or laptop computer. Such charging methods work quite well, but some user's may prefer to wear their wearable electronic devices all day and not take the devices off for the time it takes to charge the battery with a docking station or similary device. Additionally, some functions performed by any given wearable electronic device may be limited or optimized such that the functions are best performed when the device is worn by the user based on the particular sensors, circuitry and other hardware of the electronic device as manufactured.

SUMMARY

Some embodiments of the invention pertain to an auxiliary electronic device that can be attached to a wearable electronic device while the wearable device is worn by a user to charge the wearable device. For example, in one embodiment an auxiliary electronic device is provided that is adapted to charge a battery of a wearable electronic device worn on a user's wrist much like a watch. The auxiliary electronic device can be attached to the wearable electronic device fitting between a bottom surface of the wearable device and the user's wrist. The auxiliary electronic device can include a power source that can be connected to charging circuitry of the wearable device and transmit power to the charging circuitry to charge the wearable device's battery while the wearable device is being worn and used by the user.

An auxiliary electronic device according to one embodiment includes a housing, a power transmitting unit within the housing, and an attachment mechanism configured to attach the charger to the wearable device while the device is being worn by a user. The power transmitting unit can be configured to wirelessly transmit power to a power receiving unit of the wearable electronic device. In some embodiments, the power transmitting unit includes a battery and a transmitting coil positioned to align with a receiving coil in the power receiving unit when the charger is operatively coupled to the wearable electronic device. The power transmitting unit can further include a connector that enables the auxiliary electronic device to receive power from an external power source.

In some embodiments, the auxiliary electronic device can further include a pair of lugs that extend from opposite ends of the housing above the housing towards a center of the device charger and are adapted to fit within corresponding recesses of the wearable electronic device. Also, the auxiliary electronic device can further include one or more lenses that extends through the housing between a top surface and bottom surface of the housing. The one or more lenses can be positioned on the housing to align with sensors on the wearable electronic device enabling the sensors to operate through the one or more lenses when the auxiliary device is operatively coupled to the wearable electronic device.

In some embodiments an auxiliary electronic device is provided that is adapted to charge a wearable electronic device having first and second recesses formed in a casing of the electronic device where each recess is configured to accept a lug attached to a band that in turn can secure the wearable electronic device to a user's wrist. The device charger includes a housing, a wireless power transmitting unit within the housing, a first lug extending from a first end of the housing, and a second lug extending from a second end of the housing opposite the first end. The device charger can further include a third recess sized and shaped similar to the first recess on the wearable electronic device and a fourth recess sized and shaped similar to the third recess on the wearable electronic device. When the auxiliary electronic device is operatively coupled to the wearable electronic device and worn by a user, the housing is positioned between the wearable electronic device and the user's wrist. In some embodiments the third and fourth recesses are positioned such that when the band is attached to the auxiliary electronic device a length of a loop formed between the band and charger is within 10 mm of a length of the loop formed between the band and the wearable electronic device when the band is attached to the wearable electronic device. Additionally, in certain embodiments the housing has a generally rectangular shape with rounded corners, a length of less than 50 mm, a width of less than 42 mm and a thickness of 10 mm or less.

Some embodiments of the invention pertain to an auxiliary electronic device that attaches to a wearable electronic device while the device is worn by a user and provides additional functionality for the wearable electronic device augmenting and/or expanding the device's capabilities. For example, in one embodiment an auxiliary electronic device is provided that provides GPS functionality to a wearable electronic device. The auxiliary electronic device includes a power source, a GPS receiver and associated circuitry and communication circuitry that can transmit GPS data received by the GPS receiver to the wearable electronic device. In another embodiment, the auxiliary electronic device includes a power source that can be connected to charging circuitry of the wearable device and transmit power to the charging circuitry to charge the wearable device's battery in addition to augmenting and/or expanding the device's capabilities.

In some embodiments where the wearable electronic device has first and second recesses formed in a casing of the device and each recess is configured to accept a lug attached to a band that in turn can secure the wearable electronic device to a user's wrist, the auxiliary electronic device includes a housing, an electronic component within the housing that supplements the functionality of the wearable electronic device, and an attachment mechanism configured to attach the auxiliary electronic device to the wearable device while the device is being worn by a user. When the auxiliary electronic device is operatively coupled to the wearable electronic device and worn by a user, the housing is positioned between the wearable electronic device and the user's wrist. In some embodiments the electronic component includes at least one sensor and communication circuitry that can transmit data from the at least one sensor to the wearable electronic device. In some embodiments the attachment mechanism includes a first lug extending from a first end of the housing, and a second lug extending from a second end of the housing opposite the first end. The auxiliary electronic device can further include a third recess sized and shaped similar to the first recess on the wearable electronic device and a fourth recess sized and shaped similar to the third recess on the wearable electronic device.

The following detailed description together with the accompanying drawings in which the same reference numerals are sometimes used in multiple figures to designate similar or identical structural elements, provide a better understanding of the nature and advantages of the present invention.

Reference will now be made in detail to representative embodiments illustrated in the accompanying drawings. It should be understood that the following descriptions are not intended to limit the embodiments to any particular preferred embodiment. To the contrary, it is intended to cover alternatives, modifications, and equivalents as can be included within the spirit and scope of the described embodiments as defined by the accompanying claims.

DETAILED DESCRIPTION

Some embodiments of the invention pertain to an auxiliary electronic device that can be attached to a wearable electronic device while the device is worn by a user to charge the wearable device and thus can be referred to as a "charger" or a "charging device". The charging device can include a power source that can be connected to charging circuitry of the wearable device to transmit power to the charging circuitry and charge the wearable device's battery.

Figure 1:
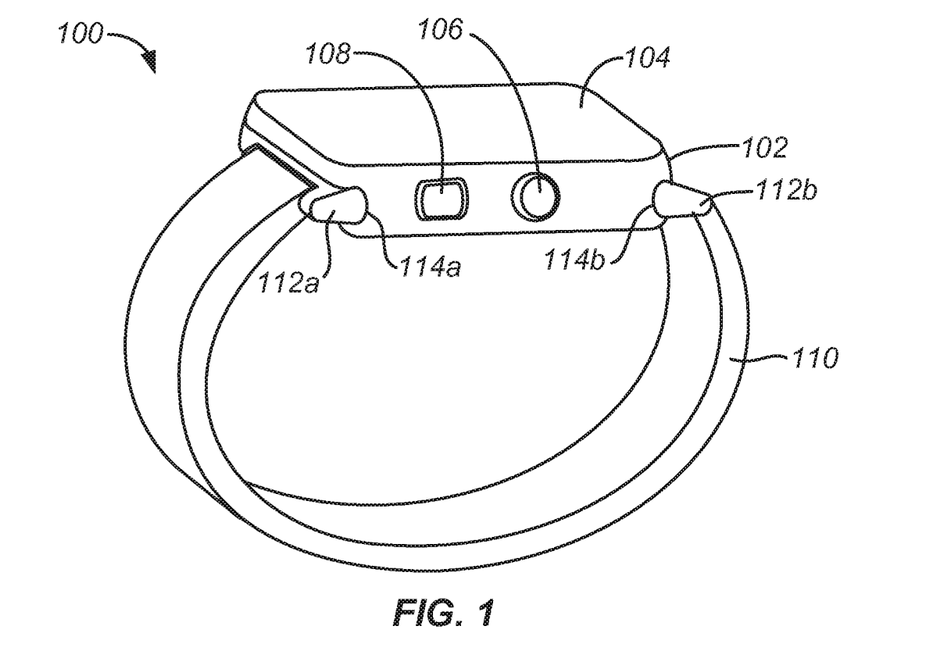
FIG. 1 is a simplified front perspective view of one type of wearable electronic device with which embodiments of the invention may be used.
Figure 2:
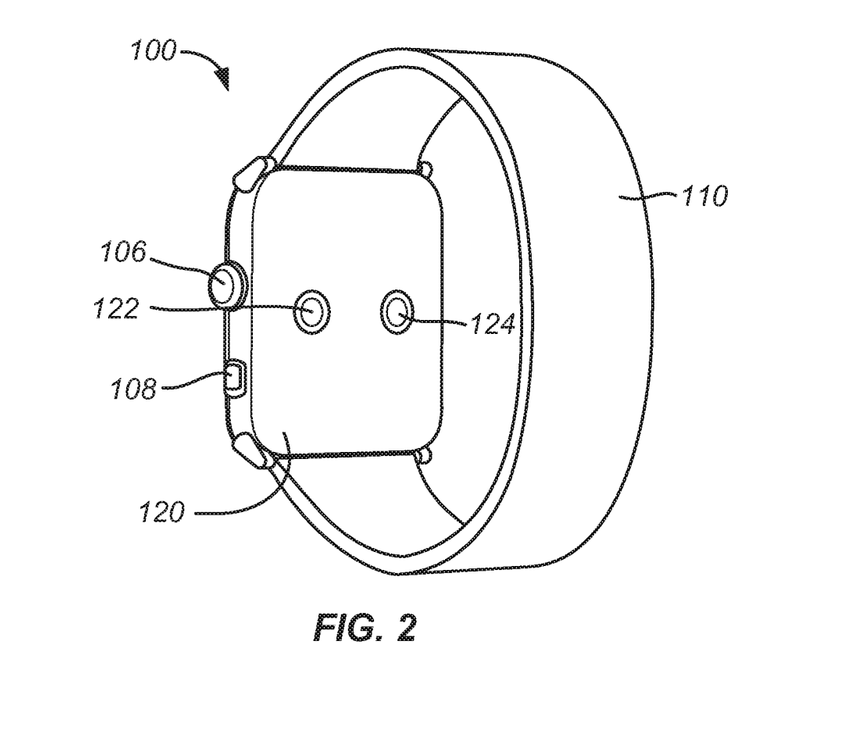
FIG. 2 is a simplified rear perspective view of the wearable electronic device shown in FIG. 1.

Embodiments of the invention may operate with one or more wearable electronic devices. One example of a suitable wearable electronic device is shown in FIGS. 1 and 2 and takes the form of a wearable electronic device 100. As shown, wearable electronic device 100 includes a casing 102 that houses a display 104 and various input devices including a dial 106 and a button 108.

Device 100 may be worn on a user's wrist and secured thereto by a band 110. Band 110 includes lugs 112a, 112b at opposing ends of the band that fit within respective recesses or apertures 114a, 114b of the casing and allow band 110 to be removeably attached to casing 102. Lugs 112a, 112b may be part of band 110 or may be separable (and/or separate) from the band. Generally, the lugs may lock into recesses 114a, 114b and thereby maintain connection between the band and casing 102. The user may release a locking mechanism (not shown) to permit the lugs to slide or otherwise move out of the recesses. In some wearable devices, the recesses may be formed in the band and the lugs may be affixed or incorporated into the casing.

Casing 102 also houses electronic circuitry (not shown in FIG. 1 or 2), including a processor and communication circuitry, along with sensors 122, 124 that are exposed on a bottom surface 120 of casing 102. The circuitry, sensors, display and input devices enable wearable electronic device 100 to perform a variety of functions including, but not limited to: keeping time; monitoring a user's physiological signals and providing health-related information based on those signals; communicating (in a wired or wireless fashion) with other electronic devices; providing alerts to a user, which may include audio, haptic, visual and/or other sensory output, any or all of which may be synchronized with one another; visually depicting data on a display; gathering data form one or more sensors that may be used to initiate, control, or modify operations of the device; determining a location of a touch on a surface of the device and/or an amount of force exerted on the device, and use either or both as input; accepting voice input to control one or more functions; accepting tactile input to control one or more functions; and so on.

A battery (not shown in FIG. 1 or 2) internal to casing 102 powers wearable electronic device 100. The battery can be recharged by an external power source, and wearable electronic device 100 can include circuitry configured to operate as a receiver in a wireless power transfer system that includes a power-transmitting component to transmit power and a power-receiving component to receive power. One example of a wireless power transfer system is an inductive power transfer system. In an inductive power transfer system, a power-receiving electronic device includes or otherwise incorporates an inductive power-receiving element configured to wirelessly receive power and/or charge one or more internal batteries. Similarly, a charging device (i.e., power transmitting component) includes or otherwise incorporates an inductive power-transmitting element configured to wirelessly transmit power to the power-receiving electronic device.

Figure 3:
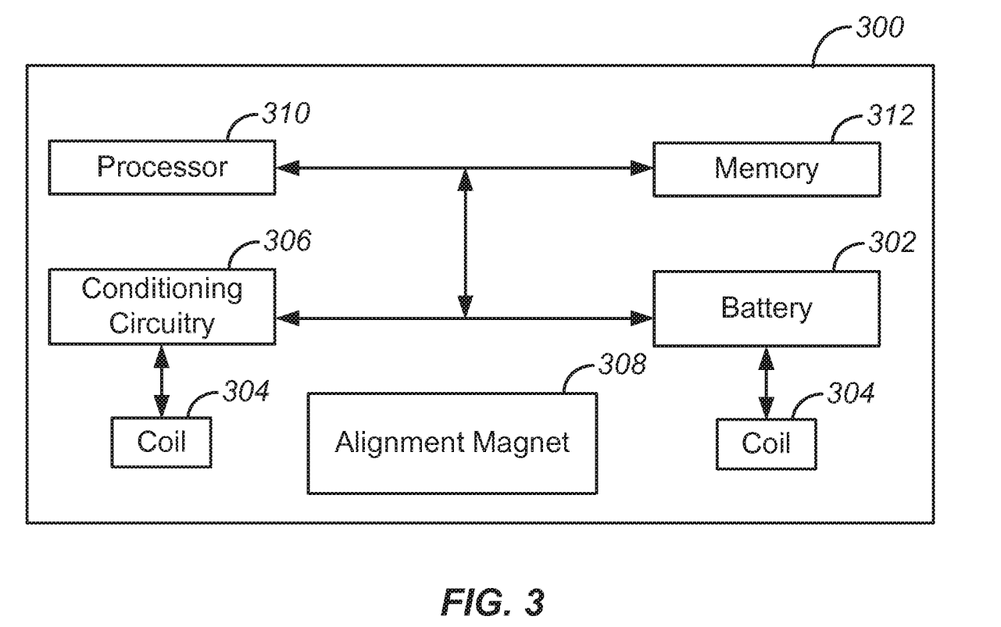
FIG. 3 is a block diagram of inductive charging circuitry and related circuitry within the wearable device shown in FIGS. 1 and 2.

FIG. 3 is a block diagram of inductive power receiving component 300 within casing 102 that, when operatively coupled with an appropriate inductive power transmitting component, can charge battery 302 within casing 102. Battery 302 is operably connected to a receive coil 304 via power conditioning circuitry 306. Receive coil 304 can be inductively coupled to a transmit coil of a charging device to receive power wirelessly from the charging device and pass the received power to battery 302 within the device 100 via power conditioning circuitry 304. Power conditioning circuitry 304 can be configured to convert the alternating current received by the receive coil 304 into direct current power for use by other components of the device. A processing unit 310 may direct the power, via one or more routing circuits and under the execution of an appropriate program residing in a memory 312, to perform or coordinate one or more functions of the device 100 typically powered by the battery 302.

Figure 4:
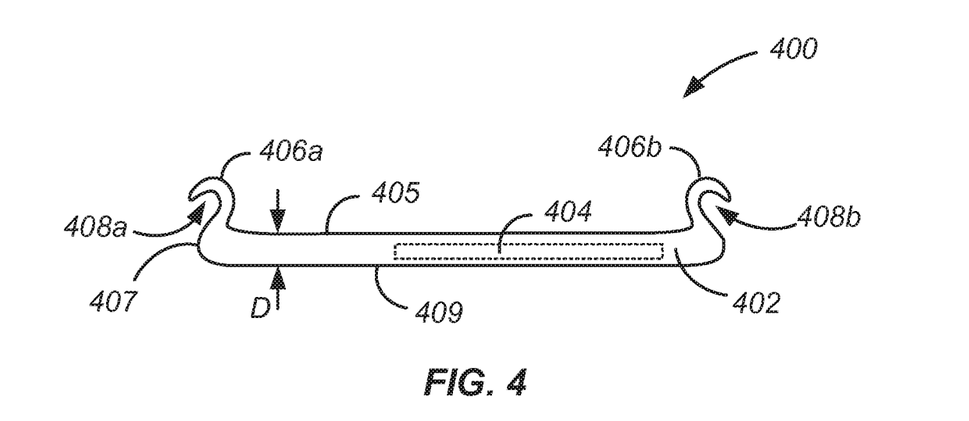
FIG. 4 is a simplified side plan view of a wearable electronic device charger according to one embodiment of the invention.
Figure 5:
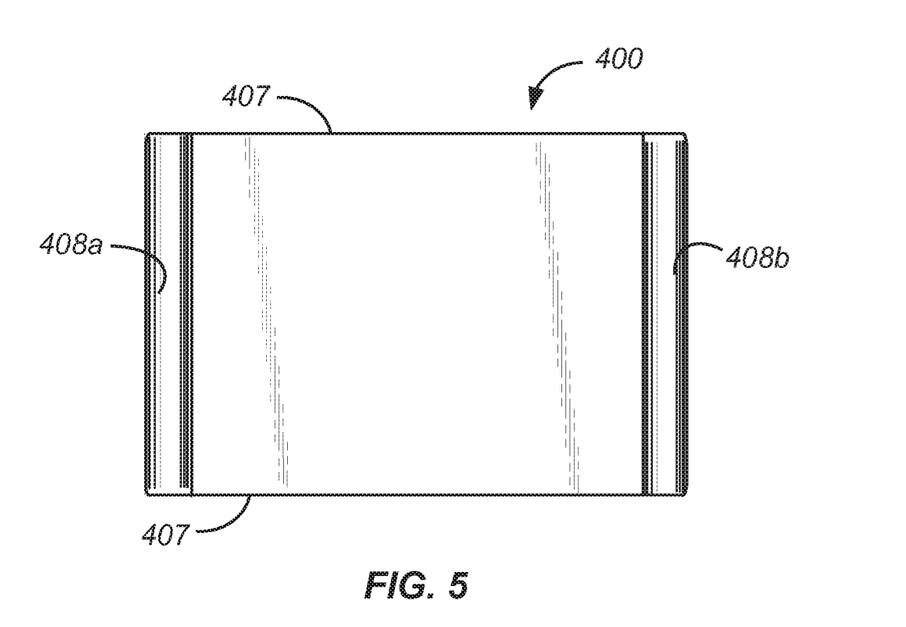
FIG. 5 is a simplified top plan view of the wearable electronic device charger shown in FIG. 4.
Figure 6:
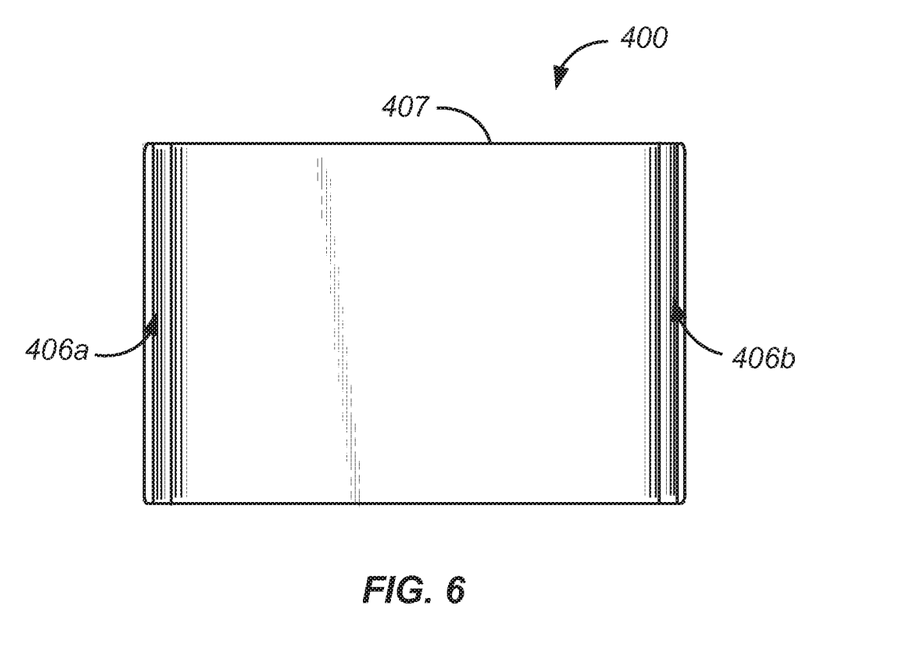
FIG. 6 is a simplified bottom plan view of the wearable electronic device charger shown in FIG. 4.

FIG. 4 is a simplified side plan view of a wearable auxiliary device 400 that can be used to charge a wearable electronic device such as device 100 shown in FIGS. 1 and 2 according to an embodiment of the invention. FIGS. 5 and 6 are a simplified top and bottom perspective views of charger 400. Auxiliary device 400 may include a relatively thin and a generally flat housing 402 that can be attached to casing 102. Housing 402 houses a power source 404 that can transmit power to device 100 to charge the rechargeable battery or other power source within the wearable electronic device.

Housing 402 can be made from a non-corrosive, chemically resistant material that is able to withstand temperature fluctuations that auxiliary device 400 will be subject to in typical use. In various embodiments housing 402 can be made from a rigid material such as metal, plastic; can be made from a flexible material, such as rubber or silicone; or can be made from a combination of such materials or other appropriate materials. In some embodiments housing 402 can be made to function as heat sink that dissipates heat generated from circuitry within housing 402 and/or from wearable electronic device 100. For example, housing 402 may designed to dissipate heat through sides 407 of the housing rather than at top surface 405 or bottom surface 409 that would be in contact with a user's skin. In one particular example, housing 402 may include a high thermal conductivity material such as graphite, copper or the like that is exposed on sides 407 and a low thermal conductivity material, such as ceramic or silicone on bottom surface 409 that abuts the user's skin. Further, in some embodiments, housing 402 may include electromagnetic shielding that blocks RF radiation and/or directs such radiation away from bottom surface 409 and thus away from the user's skin.

In certain embodiments, housing 402 can be water resistant to a depth of at least 5 meters, to a depth of at least 10 meters or up to a deep sea diving depth, such as 300 meters. In some embodiments housing 402 can be sized in its length and width dimensions similarly to the wearable electronic device 100 that charger 400 is adapted to charge. For example, in one embodiment where wearable electronic device 100 has a length of approximately 38 mm and a width of approximately 32.4 mm, housing 402 can have a length of less than 46 mm (and between 30 and 46 mm in some instances) and a width of less than 38 mm (and between 26 and 38 mm in some instances). In another embodiment where electronic device 100 has a length of approximately 42 mm and a width of approximately 36.4 mm, housing 402 can have a length of less than 50 mm (and between 34 and 50 mm in some instances) and a width of less than 42 mm (and between 30 and 42 mm in some instances). Housing 402 can also be relatively thin so that it may be comfortably worn by a user while device 100 is being worn. In one embodiment where wearable electronic device 100 is approximately 12.6 mm thick, housing 402 can have a thickness (D) between 2 and 10 mm as shown in FIG. 4. In some embodiments, the thickness (D) of housing 402 is at least an order of magnitude less than either the length or width of the housing and/or housing 402 has a generally rectangular shape with rounded corners.

In the depicted embodiment, auxiliary device 400 is attached to casing 102 in essentially the same manner that band 110 can be attached to casing 102. Specifically, charger 400 includes first and second lugs 406a, 406b that protrude from an upper surface 405 of the housing at opposite ends. Each of lug 406a, 406b project above surface 405 and towards a center of housing 402 such that the two lugs face each other. Lugs 406a, 406b can fit within and lock into recesses 114a, 114b of device 100 and thereby maintain connection between the auxiliary device 400 and casing 102. Lugs 406a, 406b can be made from the same material as housing 402 or can be made from a different material. In some embodiments, lugs 406a, 406b are made from a hard, strong metal such as stainless steel.

Auxiliary device 400 further includes first and second recesses 408a, 408b positioned adjacent to lugs 406a, 406b, respectively, that mimic recesses 114a, 114b of casing 102. Each recess 408a, 408b has an opening where a line that bisects the opening has an angle with respect to surface 405 that is approximately the same angle that each of lugs 406a, 406b extend from surface 405 at, and in one embodiment, the angles are within five degrees of each other. Recesses 408a, 408b enable band 110 to be attached to housing 402 instead of casing 102 via lugs 112a, 112b of the band. In some embodiments, recesses 408a, 408b are positioned such that band 110 can be attached to charger 400 in approximately the same position that the band would be attached to recesses 114a, 114b. Thus, a length of band 110 would not need to be adjusted to obtain the same fit on a user regardless as to whether the band is attached to charger 400 or to casing 102. For example, in one embodiment, when the band is attached to charger 400 the length of the loop formed between band 110 and charger 400 is within 10 mm of the length of the loop formed between band 110 and casing 102 when the band is attached to the casing. In another embodiment, the two configurations have loops lengths that are within 5 mm of each other.

In some embodiments, auxiliary device 400 can include both a locking mechanism and a release mechanism to enable band 110 to be secured to and easily detached from the wearable auxiliary device. The locking and release mechanisms can be operatively coupled to recesses 408a, 408b and similar or identical to the locking and release mechanisms included in device 100. Because band 110 can be readily detached from auxiliary device 400 and from casing 102, a user may change combinations of bands and/or casings, thereby permitting mixing and matching of the two categories. Auxiliary device 400 can work with different combinations of bands and casing and can be part of and extend an ecosystem of bands and devices, each of which is compatible with another.

Figure 7:
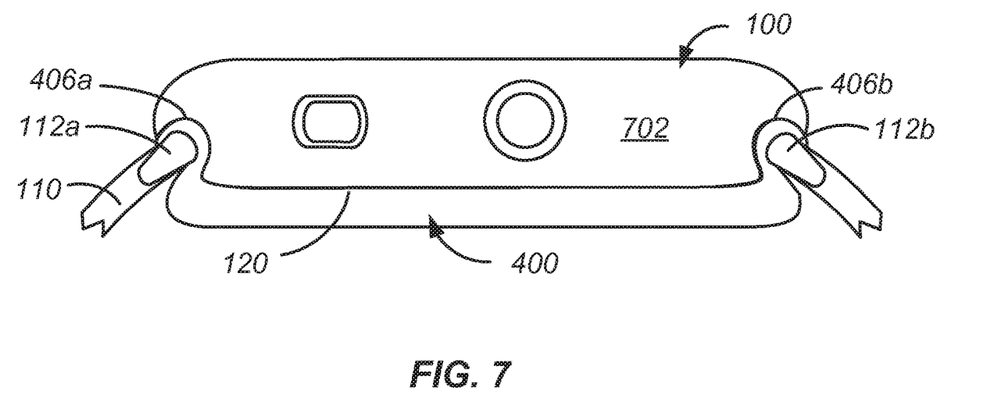
FIG. 7 is a simplified side plan view of the wearable electronic device charger shown in FIGS. 4 and 5 operatively connected to the wearable electronic device shown in FIGS. 1 and 2.

The size and shape of housing 402 in combination with lugs 406a, 406b and recesses 408a, 408b enables housing 402 to be abut the lower surface of casing 102 and be worn under wearable device 100 between the device and a user's wrist as shown in FIG. 7. Device 400 does not include a cavity or similar structure at upper surface 405 that envelops wearable device 100. Thus, there are no sidewalls on device 400 that extend from sides 407 above surface 405 to cover or partially cover side 702 of device 100 (or the side of device 100 opposite side 702 not shown in FIG. 7). In order for device In this manner, auxiliary device 400 may be thought of as a "backpack" that is worn by wearable electronic device 100 at its lower surface or back 120. In other embodiments wearable auxiliary devices are provided that can attach to a wearable electronic device at different locations and/or using different attachment mechanisms. For example, in some embodiments the auxiliary device can attach to a wearable device using one or more clips that allow it to snap onto device 100, one or more magnets that allow it to be magnetically secured to device 100 or other mechanisms or a combination of mechanisms. Also, in some embodiments the auxiliary device can attach to a top surface of a wearable device while in other embodiments the auxiliary device can attach to one or more of the side surfaces of a wearable device. In still other embodiments housing 402 may include a cavity at upper surface 405 that device 100 fits within where the sidewalls that form the cavity include cutouts to enable access to dial 106 and button 108 or any other input features on device that would otherwise be covered by the sidewalls.

Figure 8:
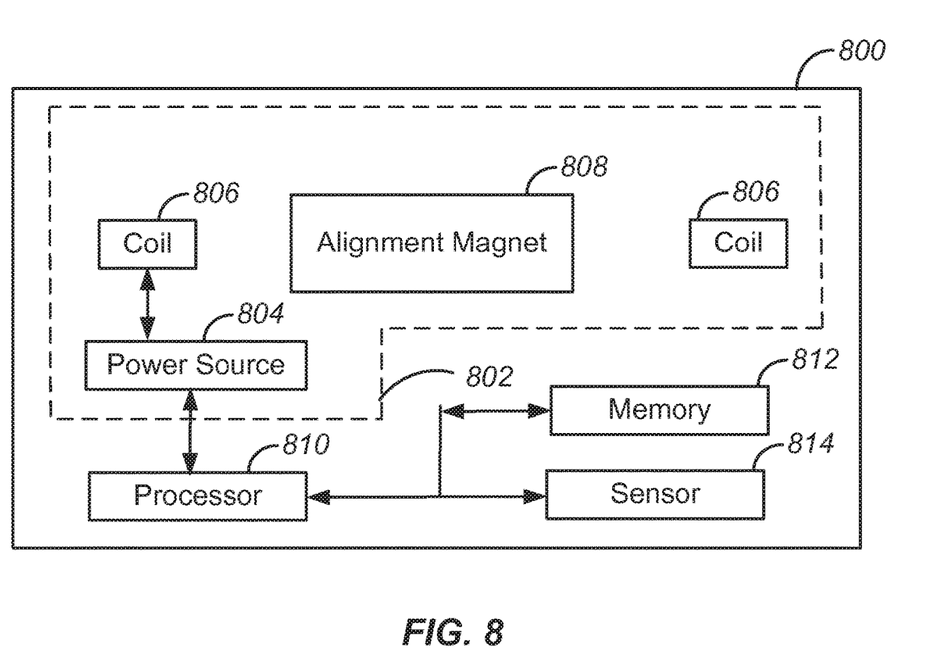
FIG. 8 is a block diagram of circuitry within a wearable electronic device charger according to an embodiment of the invention.

Power source 404 can be a replaceable battery, a rechargeable battery or a tethered power source that receives power from a source external to device 400, such as from a USB cable, Lightening cable or other wired interface. In addition to power source 404, charger 400 can include circuitry (not shown in FIGS. 4-6) within housing 402 that enables the auxiliary device to wirelessly recharge the battery, for example battery 302, of wearable device 100. FIG. 8 is a block diagram of an inductive power transmitting component 802 according to an embodiment of the invention within a wearable auxiliary device 800 (also referred to as a "wearable electronic device charger"), which can be, for example, auxiliary device 400. As shown, charging component 802 includes a power source 804, which can be power source 404, operatively coupled to a transmit coil 806 to transmit power to the device wearable electronic device 100 via electromagnetic induction or magnetic resonance. Transmit coil 806 can be an electromagnetic coil that produces a time-varying electromagnetic flux to induce a current within an electromagnetic coil within an electronic device (e.g., coil 304). The transmit coil may transmit power at a selected frequency or band of frequencies. In one example the transmit frequency is substantially fixed, although this is not required. For example, the transmit frequency may be adjusted to improve power transfer efficiency for particular operational conditions. More particularly, a high transmit frequency may be selected if more power is required by the accessory and a low transmit frequency may be selected if less power is required by the accessory. In other examples, transmit coil 806 may produce a static electromagnetic field and may physically move, shift, or otherwise change its position to produce a spatially-varying electromagnetic flux to induce a current within the receive coil.

When auxiliary device 800 is operatively attached to wearable electronic device 100, the device 100 may use the received current to replenish the charge of its rechargeable battery or to provide power to operating components associated with the electronic device. Thus, when auxiliary device 800 is operatively attached to wearable electronic device 100, the auxiliary device may wirelessly transmit power at a particular frequency via transmit coil 806 to receive coil 304 of the electronic device.

Transmit coil 806 can be positioned within the housing of auxiliary device 800 such that it aligns with receive coil 304 in wearable device 100 along a mutual axis when charger 800 is operatively attached to wearable electronic device 100. If misaligned, the power transfer efficiency between the transmit coil and the receive coil may decrease as misalignment increases. When the housing of auxiliary device 800 is similar to housing 402 which includes lugs 404a, 404b, proper alignment can be achieved when lugs 404a, 404b are interlocked within recesses 114a, 114b.

In some embodiments, one or more alignment assistance features in addition to or instead of lugs 404a, 404b can be incorporated into auxiliary device 800 to facilitate alignment of the transmit and receive coils along the mutual axis can be employed. As one example, an alignment magnet 808 can be included in auxiliary device 800 that magnetically mates with alignment magnet 308 of wearable device 100 to facilitate proper alignment of auxiliary device 800 and device 100. Additionally, the top and bottom surfaces of auxiliary device 800 and wearable device 100, respectively, may cooperate to further facilitate alignment. For example, in one embodiment a bottom surface of wearable device 100 is convex and a top surface of charger 800 (e.g., surface 405) is concave, following the same curvature as the bottom surface of device 100. In this manner, the complementary geometries may facilitate alignment of the device charger and wearable device in addition to one or both of lugs 404a, 404b and/or alignment magnet 808.

Auxiliary device 800 may also include a processor 810 that may be used to control the operation of or coordinate one or more functions of the charger. In some embodiments, auxiliary device 800 may also include one or more sensors 812 to determine whether wearable electronic device 100 is present and ready to receive transmitted power from the charger. For example, auxiliary device 800 may include an optical sensor, such as an infrared proximity sensor. When auxiliary device 800 is attached to device 100, the infrared proximity sensor may produce a signal that processor 810 uses to determine the presence of device 100. Processor 810 may, optionally, use another method or structure to verify the presence of the accessory via sensor 812. Examples of different sensors that may be suitable to detect or verify the presence of device 100 may include a mass sensor, a mechanical interlock, switch, button or the like, a Hall effect sensor, or other electronic sensor. Continuing the example, after sensor 812 reports that the device 100 may be present, the processor 810 may activate a communication channel to attempt to communicate with the device 100.

Some embodiments of the invention may include a wired interface for charging battery 302 and/or for exchanging data with wearable electronic device 100. The wired interface may be in addition to or instead of a wireless interface. For example, in one embodiment device 400 may include contacts in or near lugs 112a, 112b that are sized and positioned to physically and electrically couple to one or more contacts on the wearable electronic device. The contacts may include one or more power contacts as well as one or more data contacts, such as a pair of differential data contacts. In another embodiment, the one or more contacts may be on an upper surface of device 400 and positioned to physically and electrically couple to corresponding contacts on a bottom surface of wearable device 100. Thus, when device 400 is operatively attached to wearable device 100 the contacts are not visible on either device.

Figure 9:
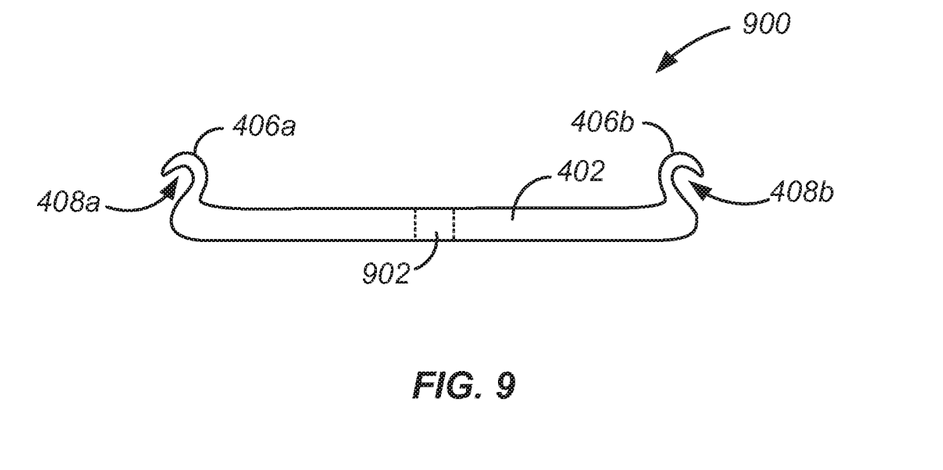
FIG. 9 is a simplified side plan view of a wearable electronic device charger according to another embodiment of the invention.
Figure 10:
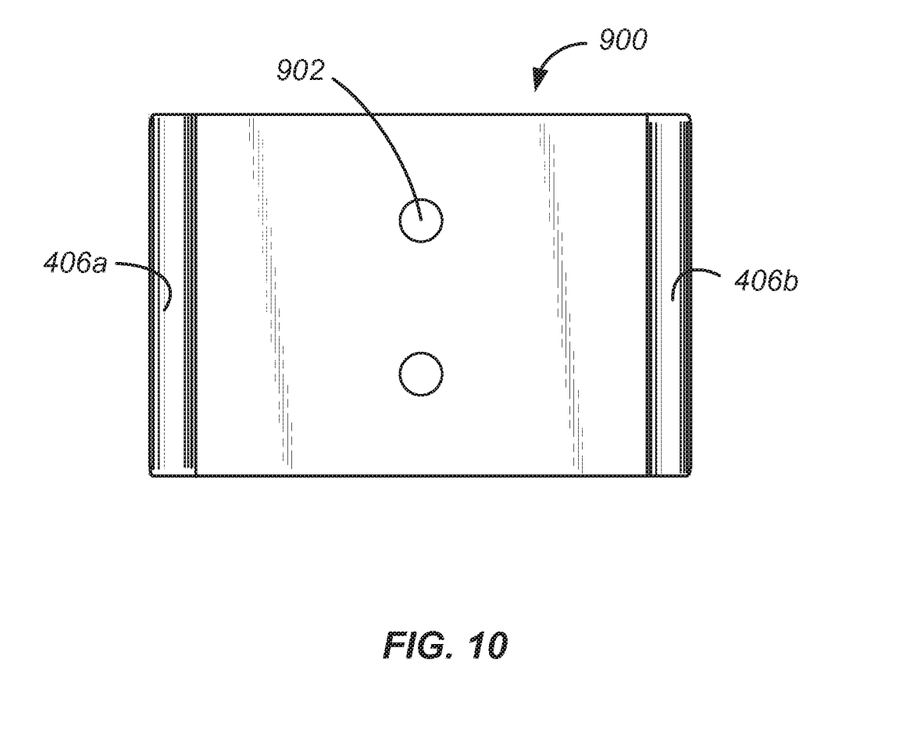
FIG. 10 is a simplified top plan view of a wearable electronic device charger according to the embodiment shown in FIG. 9.

FIG. 9 is a simplified side plan view of a wearable auxiliary device 900 according to another embodiment of the invention, and FIG. 10 is a simplified top plan view auxiliary device 900. Auxiliary device 900 is similar to auxiliary device 400 but includes one or more lenses 902 that traverse the thickness of housing 402 and enable optical sensors within device 100 to properly function while auxiliary device 900 is operatively connected to device 100. For example, in the embodiment depicted in FIGS. 9 and 10, auxiliary device 900 includes two lenses 902, each of which is aligned with one of sensors 122, 124 in device 100. Sensors 122, 124 can be, for example, infrared and visible light LEDs and photodiodes that sense one or more biometric measurements of a user. When auxiliary device 900 is used with device 100 and worn by a user, the lenses 902 enable the sensors 122, 124 to capture information from the skin of the user where housing 402 of auxiliary device 900 would otherwise interfere with or prevent the sensors from being properly used. In some embodiments, each lens 902 may magnify, amplify or otherwise enhance the ability of sensors 122, 124 to capture such data. In another particular embodiment four sensors are exposed on bottom surface 120 of device 100 and auxiliary device 900 includes four lenses 902, one for each sensor.

Figure 11:
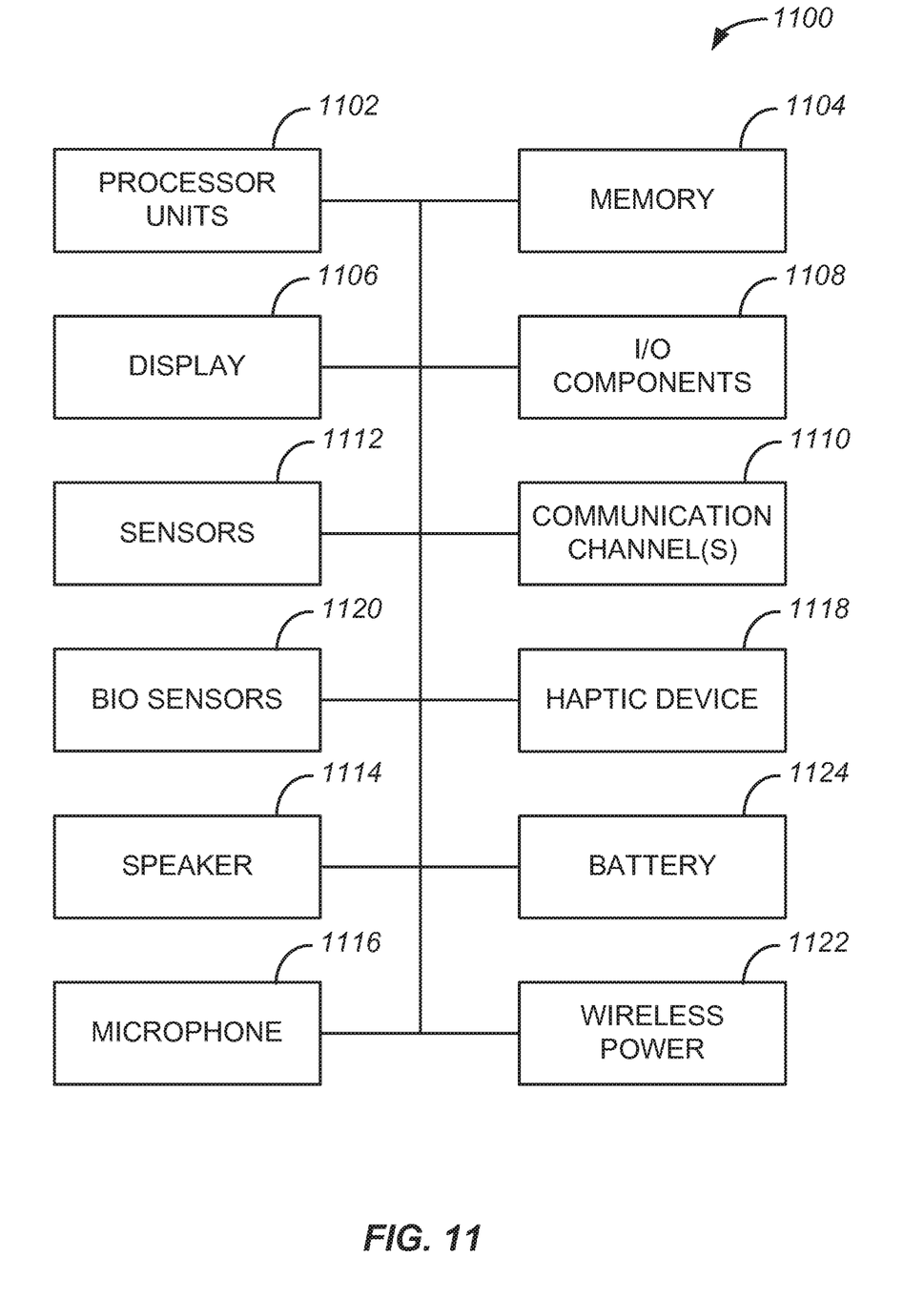
FIG. 11 is a schematic diagram of a wearable electronic device with which embodiments of the invention may be used.

As previously mentioned, embodiments of the invention can be used to charge a variety of wearable electronic devices in addition to the particular wrist-worn electronic devices discussed above. FIG. 11 is a schematic diagram of a wearable electronic device 1100, such as device 100 shown in FIGS. 1 and 2, with which embodiments of the invention may be used. As shown in FIG. 11, the device 1100 includes one or more processing units 1102 that are configured to access a memory 1104 having instructions stored thereon. The instructions or computer programs may be configured to perform one or more of the operations or functions described with respect to the device 1100. For example, the instructions may be configured to control or coordinate the operation of the various components of the device. Such components include, but are not limited to, display stack 1106, one or more input/output components 1108, one or more communication channels 1110, one or more sensors 1112, a speaker 1114, microphone 1116, and/or one or more haptic feedback devices 1118. In some embodiments the speaker and microphone may be combined into a single unit and/or may share a common port through a housing of the device.

The processing units 1102 of FIG. 2 may be implemented as any electronic device capable of processing, receiving, or transmitting data or instructions. For example, the processing units 1102 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

Display stack 1106 may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments. Display stack may also include one or more touch sensors to determine a location of a touch on the cover glass. The touch sensor may be self-capacitive in certain embodiments, mutual-capacitive in others, or a combination thereof.

Similarly, device 1100 may include a force sensor to determine an amount of force applied to the cover glass. The force sensor may be a capacitive sensor in some embodiments and a strain sensor in other embodiments. In either embodiment, the force sensor is generally transparent and made form transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

Wearable electronic device 1100 may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic and/or visual components of the alert may be synchronized to provide an overall experience to a user. One or more components may be delayed relative to other components to create a desired synchronization between them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output but at a weak or even subliminal level, thereby priming the wearer to receive the auditory output.

The example electronic device may communicate with other electronic devices either through a wired connection or wirelessly via communication channels 1110. Data may be passed between devices, permitting one device to relay information to another; control another; employ another's sensors, outputs, and/or inputs; and so on.

Some embodiments of the invention can charge a wearable device, such as device 100 or device 1100, as discussed above. Additionally, some embodiments of the invention can provide additional functionality to the wearable device instead of, or in addition to, charging the wearable device. For example, in one embodiment an auxiliary electronic device is provided that can attach to a wearable electronic device using any of the techniques discussed above and can provide GPS capabilities to the wearable electronic device in addition to or instead of charging the device. In other embodiments, an auxiliary electronic device according to the invention can include any of the sensors or functionality discussed above with respect to FIG. 11 such as additional haptic functionality, one or more ECR sensors, one or more GSR sensors, and the like.

Figure 12:
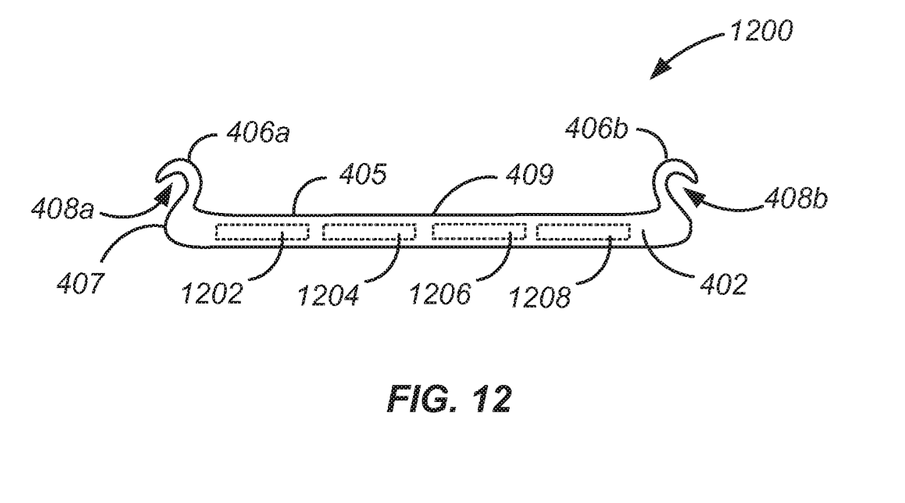
FIG. 12 is a simplified side plan view of a wearable auxiliary electronic device according to another embodiment of the invention.

FIG. 12 is a simplified side plan view of a wearable auxiliary electronic device 1200 that augments the functionality of a wearable electronic device, such as device 100 shown in FIGS. 1 and 2 according to an embodiment of the invention. As shown in FIG. 12, device 1200 has the same general form factor as device 400 shown in FIG. 4. Thus, the same reference numbers used in FIG. 4 are used in FIG. 12 to refer to like components, which for the sake of brevity, are not discussed below. In other embodiments, device 1200 can have the form factor of device 900 shown in FIG. 9 or a different form factor altogether.

As shown in FIG. 12, auxiliary device 1200 includes additional components 1202, 1204, 1206 and 1208 each of which may supplement the functionality that one or more of the components shown in FIG. 11 provides for wearable device 1100. In some embodiments, one or more of components 1202, 1204, 1206 and 1208 can be an environmental sensor including an electronic, mechanical, electromechanical, optical, or other type of sensor that provides information related to external conditions around auxiliary device 1200 and thus, when device 1200 is operatively attached to wearable electronic device 1100, around device 1100 as well. For example, if a particular wearable device did not include a temperature sensor to measure ambient air temperature, an auxiliary electronic device 1200 according to an embodiment of the invention may include a sensor 1202 that is a temperature sensor. Similarly, if a particular wearable device did not include a speaker and/or a microphone, an auxiliary electronic device 1200 according to an embodiment of the invention may include one or more audio devices 1204 to provide this functionality. As still another example, a Global Positioning System (GPS) sensor 1206 may be included within housing 402 that can determine location based on signals received from GPS satellites and collect GPS data for a wearable electronic device that does not have such a sensor. Auxiliary electronic device 1200 can provide any and all such collected sensor data, including GPS data, over a communication channel provided by communication circuitry 1208 to a wearable device 1100 via communication channel 1110. Any type and combination of environmental sensors can be used as one or more of components 1202, 1204, 1206 and 1208. Other specific examples of appropriate sensors include an accelerometer that can sense acceleration (relative to free fall) along one or more axes, e.g., using piezoelectric or other components in conjunction with associated electronics to produce a signal; a magnetometer that can sense an ambient magnetic field (e.g., Earth's magnetic field) and generate a corresponding electrical signal, which can be interpreted as a compass direction; a gyroscope that can sense rotational motion in one or more directions; a proximity sensor; an ambient light sensor; physiological or biometric sensors, such as pulse sensors, ECG sensors, or the like; among other sensors.

Auxiliary electronic device 1200 can communicate with device 1100 using a wired interface or a wireless interface. As one example, a wired connection can be made by matching male and female connectors, one on device 1100 and one on device 1200 (neither of which is shown), that physically and electrically mate when auxiliary electronic device 1200 is attached to device 1100. In some embodiments where auxiliary device 1200 attaches to a bottom surface of device 1100, the connector for device 1100 can be on the bottom surface of the device and the connector for auxiliary electronic device 1200 can be on the top surface of the auxiliary electronic device so that neither connector is visible when the two devices are operatively connected. As another example, a wireless connection can be made between the auxiliary electronic device 1200 and device 1100 using a low power communication protocol, such as the BTLE (BlueTooth Low Energy) protocol, or another appropriate protocol. Processor 1102 can then process any sensor data collected by components 1202, 1204, 1206 and 1208 and transmitted to device 1100 (e.g., on a streaming basis or in response to polling by processor 1102 as desired) and display the data and related information on display stack 1106 for the user to view.

While not shown in FIG. 12, device 1200 may include a power transmitting component, such as power source 404 described above that enables device 1200 to charge wearable electronic device 1100, along with other components. For example, while not shown in FIG. 12, device 1200 may include a processor that controls various functions and features of device 1200 along with a memory that stores computer-readable instructions executable by the processor as well as sensor information and/or other data. In various embodiments, auxiliary device 1200 can include some, but not each, of components 1202, 1204, 1206 and 1208, and in other embodiments device 1200 can include one or more of components 1202, 1204, 1206 and 1208 as well as other components.

Figure 13:
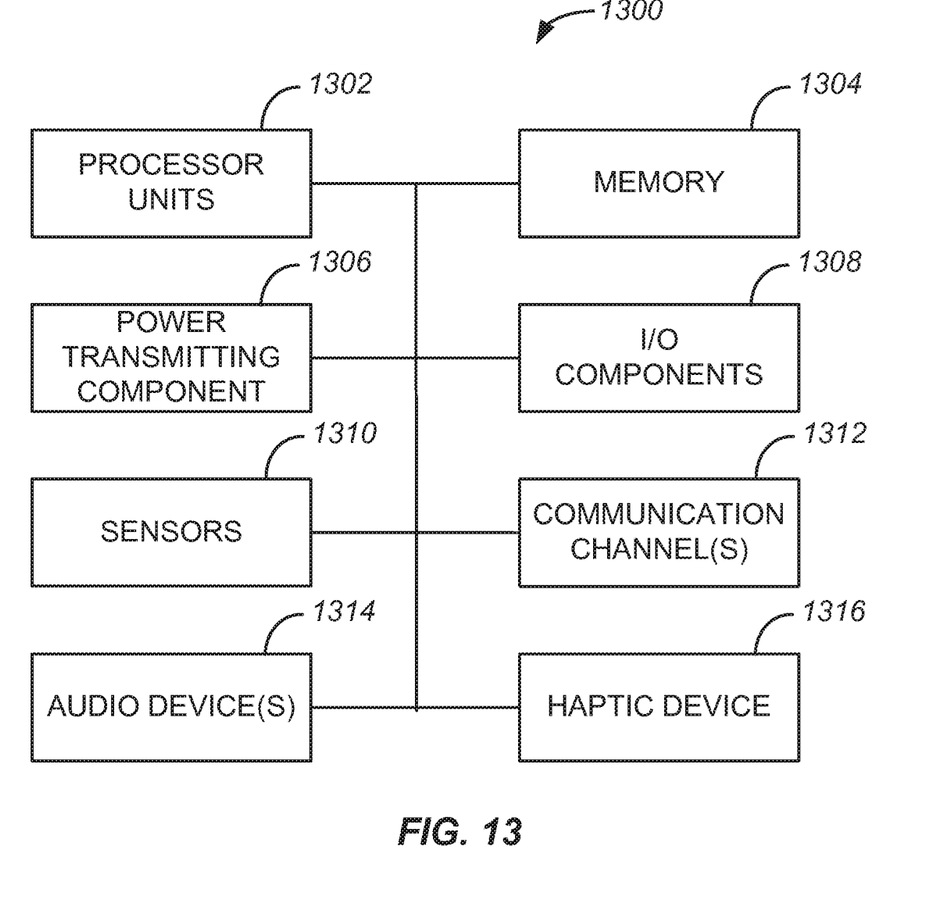
FIG. 13 is a schematic diagram of a wearable auxiliary electronic device according to still another embodiment of the invention.

FIG. 13 is a schematic diagram of an auxiliary electronic device 1300 for a wearable electronic device according to an embodiment of the invention, which can be similar to device 1200. As shown in FIG. 13, auxiliary electronic device 1300 can include a processor 1300, a memory 1304 that are similar to processor 710 and memory 812 discussed above with respect to FIG. 8. Auxiliary electronic device 1300 may also optionally include a power transmitting component 1306 similar to power transmitting component 802 and may further include any or all of the following: one or more I/O components 1308, sensors 1310, communication channels 1312, audio devices 1314, and a haptic device 1316. I/O components 1308, sensors 1310, communication channels 1312 and haptic device 1316 can be any of the same named devices discussed above with respect to wearable electronic device 1100. Similarly, audio devices 1314 can be one or more speakers and/or a microphone as described above with respect to speaker 1114 and microphone 1116. When included in auxiliary electronic device 1300, each of these additional components can perform functionality that supplements the functionality of the wearable electronic device that the auxiliary device is paired with.

The foregoing description, for purposes of explanation, used specific nomenclature to provide a thorough understanding of the described embodiments. However, it will be apparent to one skilled in the art that the specific details are not required in order to practice the described embodiments. For example, while several specific embodiments of the invention described above use inductive coupling to wirelessly transmit power to a wearable electronic device, the invention is not limited to any particular wireless power transfer technique and other near-field or non-radiative wireless power transfer techniques as well as radiative wireless power transfer techniques can be used in some embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. An auxiliary device for a watch, the watch including watch recesses on opposing ends of the watch to accept band lugs of a band that secures the watch to a user's wrist, the auxiliary device comprising:
    a housing sized and shaped to fit between the watch and a user's wrist while the watch is secured to the user with the band;
    an attachment mechanism including auxiliary device lugs each having a size and shape to fit within a respective one of the watch recesses of the watch to attach the housing to the watch; and
    an electronic component within the housing configured to interact with an electronic component within the watch while the auxiliary device is attached to the watch by the attachment mechanism.

2. The auxiliary device of claim 1, wherein the auxiliary device further comprises auxiliary device recesses each having a size and shape similar to the size and shape of the watch recesses to accept one of the band lugs within a corresponding one of the auxiliary device recesses.

3. The auxiliary device of claim 1, wherein the electronic component comprises a sensor and communication circuitry that can transmit data from the sensor to the watch.

4. The auxiliary device of claim 1, wherein the electronic component comprises a wireless power transmitting unit configured to wirelessly transmit power to a power receiving unit of the watch and comprising a battery and a transmitting coil positioned to align with a receiving coil in the power receiving unit when the auxiliary device is operatively coupled to the watch.

5. The auxiliary device of claim 1, wherein the electronic component comprises an input/output component, a speaker, a microphone, or a haptic feedback device.

6. The auxiliary device of claim 1, wherein the auxiliary device further comprises a passage extending through the housing and positioned such that, while the watch is being worn by a user, the passage is aligned with a sensor of the watch to allow the sensor to operate through the passage.

7. The auxiliary device of claim 1, wherein the housing comprises a concave surface that conforms to a convex surface of the watch.

8. An auxiliary device for a watch, the watch including a watch recess having a size and shape to accept a band lug of a band to secure the watch to a user's wrist, the auxiliary device comprising:
    a housing;
    an electronic component within the housing;
    an auxiliary device lug extending from the housing and configured to be accepted within the watch recess; and
    an auxiliary device recess having a size and shape similar to the size and shape of the watch recess to accept the band lug within the auxiliary device recess.

9. The auxiliary device of claim 8, wherein:
    the auxiliary device recess is a first auxiliary device recess;
    the watch recess is a first watch recess;
    the band lug is a first band lug; and
    the auxiliary device further comprises a second auxiliary device recess having a size and shape similar to the size and shape of a second watch recess of the watch to accept a second band lug within the second auxiliary device recess.

10. The auxiliary device of claim 8, wherein the electronic component comprises a sensor and communication circuitry that can transmit data from the sensor to the watch.

11. The auxiliary device of claim 8, wherein the electronic component comprises a wireless power transmitting unit configured to wirelessly transmit power to a power receiving unit of the watch and comprising a battery and a transmitting coil positioned to align with a receiving coil in the power receiving unit when the auxiliary device is operatively coupled to the watch.

12. The auxiliary device of claim 8, wherein the electronic component comprises an input/output component, a speaker, a microphone, or a haptic feedback device.

13. The auxiliary device of claim 8, wherein the auxiliary device further comprises a passage extending through the housing and positioned such that, while the watch is being worn by a user, the passage is aligned with a sensor of the watch to allow the sensor to operate through the passage.

14. The auxiliary device of claim 8, wherein the housing sized and shaped to fit between the watch and a user's wrist while the watch is secured to the user with the band.

15. The auxiliary device of claim 8, wherein the housing comprises a concave surface that conforms to a convex surface of the watch.

16. An auxiliary device for a watch, the watch including a sensor, the auxiliary device comprising:
    a housing sized and shaped to fit between the watch and a user's wrist while the watch is worn by the user;
    an electronic component within the housing configured to interact with an electronic component of the watch; and
    a passage extending through the housing and positioned such that, while the watch is being worn by a user, the passage is aligned with the sensor of the watch to allow the sensor to operate through the passage.

17. The auxiliary device of claim 16, further comprising a lens positioned within the passage to allow the sensor to operate through the lens.

18. The auxiliary device of claim 16, wherein:
    the sensor is a first sensor;
    the watch includes a second sensor;
    the passage is a first passage; and
    the auxiliary device further comprises a second passage extending through the housing and positioned such that, while the watch is being worn by a user, the second passage is aligned with the second sensor of the watch to allow the second sensor to operate through the second passage.

19. The auxiliary device of claim 16, wherein the electronic component comprises a wireless power transmitting unit configured to wirelessly transmit power to a power receiving unit of the watch and comprising a battery and a transmitting coil positioned to align with a receiving coil in the power receiving unit when the auxiliary device is operatively coupled to the watch.

20. The auxiliary device of claim 16, wherein the electronic component comprises an input/output component, a speaker, a microphone, or a haptic feedback device.

\* \* \* \* \*